(12) United States Patent
Wang et al.

(10) Patent No.: US 8,647,685 B1
(45) Date of Patent: Feb. 11, 2014

(54) COMPOSITE OF HERBAL EXTRACTS FOR LOWERING BLOOD LIPID AND MEDICATION COMPRISING THE SAID COMPOSITE

(75) Inventors: Po-Lun Wang, Taipei (TW); I-Min Liu, Kaohsiung (TW); Shorong-Shii Liou, Kaohsiung (TW); Chia-Ju Chang, Kaohsiung (TW)

(73) Assignee: Timing Pharmaceutical Co., Ltd., New Taipei (TW)

( * ) Notice: Subject to any disclaimer, the term of this patent is extended or adjusted under 35 U.S.C. 154(b) by 7 days.

(21) Appl. No.: 13/566,825

(22) Filed: Aug. 3, 2012

(51) Int. Cl.
*A61K 36/00* (2006.01)
*A61K 36/254* (2006.01)
*A61K 36/896* (2006.01)

(52) U.S. Cl.
USPC .......................................... 424/725; 424/728

(58) Field of Classification Search
None
See application file for complete search history.

(56) References Cited

U.S. PATENT DOCUMENTS

| | | | |
|---|---|---|---|
| 6,541,046 B2 | 4/2003 | Wei et al. | |
| 7,736,675 B2 | 6/2010 | Oben | |
| 2008/0026084 A1 | 1/2008 | Subbiah | |

FOREIGN PATENT DOCUMENTS

TW  200920390 A  5/2009

*Primary Examiner* — Qiuwen Mi
(74) *Attorney, Agent, or Firm* — Muncy, Geissler, Olds & Lowe, PLLC (57) ABSTRACT

A composite of herbal extracts comprises an extract of *Eucheuma okamurai* Yamada in a weight ratio of 33.4%-77.7%; an extract of *Acanthopanax senticosus* in a weight ratio of 11.14%-33.3%; and an extract of *Dioscorea alata* in a weight ratio of 11.14%-33.3%. Furthermore, a medication for lowering blood lipid, comprising the said composite of herbal extracts and a pharmaceutical acceptable carrier or excipient, is also disclosed.

14 Claims, 5 Drawing Sheets

COMPOSITE OF HERBAL EXTRACTS FOR LOWERING BLOOD LIPID AND MEDICATION COMPRISING THE SAID COMPOSITE

BACKGROUND OF THE INVENTION

1. Field of the Invention

The present invention generally relates to a composite of herbal extracts and, more particularly, to a composite of herbal extracts apt to lower blood lipid and a medication comprising the said composite.

2. Description of the Related Art

Since social environment has changed from agricultural economy to industrial economy, peoples' activity decrease and dietary habit changes, resulting in over intake of calorie and fat-accumulation. Accordingly, hyperlipidemia becomes a general disease to people nowadays. Hyperlipidemia refers to abnormally elevated levels of lipids or lipoproteins in blood. When fat accumulates in bodies, it will lead to fatty liver or, even complicating stroke, atherosclerosis, heart diseases, or other brain-cardiovascular diseases. It is noted that hyperlipidemia plays an important role in the progressing of brain-cardiovascular diseases, and therefore it is necessary to control the levels of blood lipids, so as to reduce incidences to brain-cardiovascular diseases.

In conventional arts, levels of blood lipid can be well controlled if a preferable herbal medication is given according to various types of hyperlipidemia, besides changing a preferable life style by decreasing the intake of caroler or increasing exercises.

Generally, *Savia miltiorrhiza*, *Fructus ligustri* Lucidi, and *Carthami flos* all have efficacies on avoiding fat-accumulation. Also, a significant amount of commercial food products or herbal medications are apt to lower blood lipids, such as oats, *Ganodorma lucidum*, *Eucheuma okamurai* Yamada, *Acanthopanax senticosus* or *Dioscorea alata*. However, due to a poor amount of active substances in each food product or herbal medication, those food products or herbal medications may be insufficient in lowering blood lipid.

For improving the said issue, the food products or herbal medications are further processed to extract the active substances therein. As an example, TW Patent Publication entitled "oil soluble extract of Chinese herbs having the ability to modulate blood lipid," discloses an oil soluble extracts obtained from extracts of *Myristica fragrans*, *Glycyrrhizae radix*, *Ligusticum chuanxiong*, *Schizandrae fructus*, *Crataegus*, *Angelicae sinonsis Radix*, *Savia miltiorrhiza*, *Atractylodes macrocephala*, *Panax notoginseng*, *Rehmannia glatinosa*, *Dioscorea opposita*, *Eucommiae cortex*, *Ginkgo biloba*, *Chenpi*, *Pueraria*, *polygonatum sibricum*, *Lycium chinense miller*, *Portulaca oleracea* Linn, *Cassia obtusifolia*, or a combination thereof. However, the said oil soluble extracts comprises various contents, which may interfere with each others, affecting the ability of the said oil soluble extracts on modulating blood lipid. Therefore, it is needed to provide a new herbal product, apt to lower blood lipid effectively.

SUMMARY OF THE INVENTION

It is therefore the objective of this invention to provide a composite of herbal extracts for lowering blood lipid, which can reduce incidence to cardiovascular disease.

It is therefore the further objective of this invention to provide a composite of herbal extracts for lowering blood lipid, comprising three different herbal extracts, with each herbal extract cooperating with each other to achieve significant effects on lowering blood lipid via synergism.

A composite of herbal extracts comprises an extract of *Eucheuma okamurai* Yamada in a weight ratio of 33.4%-77.7%; an extract of *Acanthopanax senticosus* in a weight ratio of 11.14%-33.3%; and an extract of *Dioscorea alata* in a weight ratio of 11.14%-33.3%.

In the composite of herbal extracts for lowering blood lipid, the extract of *Eucheuma okamurai* Yamada, the extract of *Acanthopanax senticosus* and the extract of *Dioscorea alata* are obtained by using a method comprising: extracting samples of *Eucheuma okamurai* Yamada, *Acanthopanax senticosus* and *Dioscorea alata* respectively with a solvent, with the solvent and anyone of the samples of *Eucheuma okamurai* Yamada, *Acanthopanax senticosus* and *Dioscorea alata* being 1 to 8-12 in a volume ratio thereof, to obtain a liquid extract of *Eucheuma okamurai* Yamada, a liquid extract of *Acanthopanax senticosus* and a liquid extract of *Dioscorea alata*; and condensing the liquid extract of *Eucheuma okamurai* Yamada, the liquid extract of *Acanthopanax senticosus* and the liquid extract of *Dioscorea alata* respectively to obtain the extract of *Eucheuma okamurai* Yamada, the extract of *Acanthopanax senticosus* and the extract of *Dioscorea alata*; wherein, the solvent is water.

In the composite of herbal extracts for lowering blood lipid, the samples of *Eucheuma okamurai* Yamada, *Acanthopanax senticosus* and *Dioscorea alata* are fresh samples that have not been dried or solarized, dry samples or decocted samples.

In the composite of herbal extracts for lowering blood lipid, the sample of *Acanthopanax senticosus* in 1 kg is soaked in 200 ml huangjiu for eight hours, and then decocted at 121° C., 15 pound/itch$^2$ for one hour, to obtain a decocted sample of *Acanthopanax senticosus*.

In the composite of herbal extracts for lowering blood lipid, the sample of *Eucheuma okamurai* Yamada is lyophilized to obtain a dry sample of *Eucheuma okamurai* Yamada.

In the composite of herbal extracts for lowering blood lipid, the sample of *Dioscorea alata* is heat-dried to obtain a dry sample of *Dioscorea alata*.

In the composite of herbal extracts for lowering blood lipid, the sample of *Eucheuma okamurai* Yamada in the extracting comprises whole plant of *Eucheuma okamurai* Yamada.

In the composite of herbal extracts for lowering blood lipid, the sample of *Acanthopanax senticosus* in the said extracting comprises roots and stems of *Acanthopanax senticosus*.

In the composite of herbal extracts for lowering blood lipid, the sample of *Dioscorea alata* in the said extracting comprises root tubers of *Dioscorea alata*.

In the composite of herbal extracts for lowering blood lipid, the said extracting is processed at 40° C.-60° C.

In the composite of herbal extracts for lowering blood lipid, the said extracting is processed for six to ten hours.

A medication for lowering blood lipid comprises the composite of herbal extracts as claimed in one of claim 1 and a pharmaceutical acceptable carrier or excipient.

In the medication for lowering blood lipid, the composite of herbal extracts is in a dosage of 150-600 mg.

In the medication for lowering blood lipid, the composite of herbal extracts is in a type of pastil, capsule, powder, pellet or solution.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the terms "first", "second", "third", "fourth", "inner", "outer" "top", "bottom" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

A preferred embodiment of the invention discloses a composite of herbal extracts, which comprises extracts obtained from *Eucheuma okamurai* Yamada, *Acanthopanax senticosus* and *Dioscorea alata*, being mixed in a particular weight ratio and, particularly to comprises an extract of *Eucheuma okamurai* Yamada in a weight ratio of 33.4%-77.7%, an extract of *Acanthopanax senticosus* in a weight ratio of 11.14%-33.3% and an extract of *Dioscorea alata* in a weight ratio of 11.14%-33.3%, being dramatically beneficial in lowering total cholesterol (TC), total triglyceride (TG), and low-density lipoprotein cholesterol (LDL-C) in blood; preventing from fat-accumulation in adipocyte; and decreasing incidences to brain and cardiovascular diseases. Generally, *Eucheuma okamurai* Yamada, *Acanthopanax senticosus*, and *Dioscorea alata* are all capable of controlling blood lipid. However, in view of property of Chinese medicine, property of *Eucheuma okamurai* Yamada is cool, easily leading to poor circulation or illness in digestive system, so that *Eucheuma okamurai* Yamada is improper to apply to hyperlipidemin patents for a long-term. Then, with the cooperation of *Acanthopanax senticosus* and *Dioscorea alata*, the poor circulation caused by *Eucheuma okamurai* Yamada will be dramatically reduced, and also the cardiovascular and digestive functions can be promoted, facilitating the efficacy on lowering blood lipid.

The composite of herbal extracts of the preferable embodiment is apt to be manufactured into medication for lowering blood lipid. The said composite of herbal extracts can be combined with a pharmaceutical acceptable carrier or excipient, to form a medication in a type of pastil, capsule, powder, pellet or solution, and which is easy to be given to an individual via oral.

Figure 1:
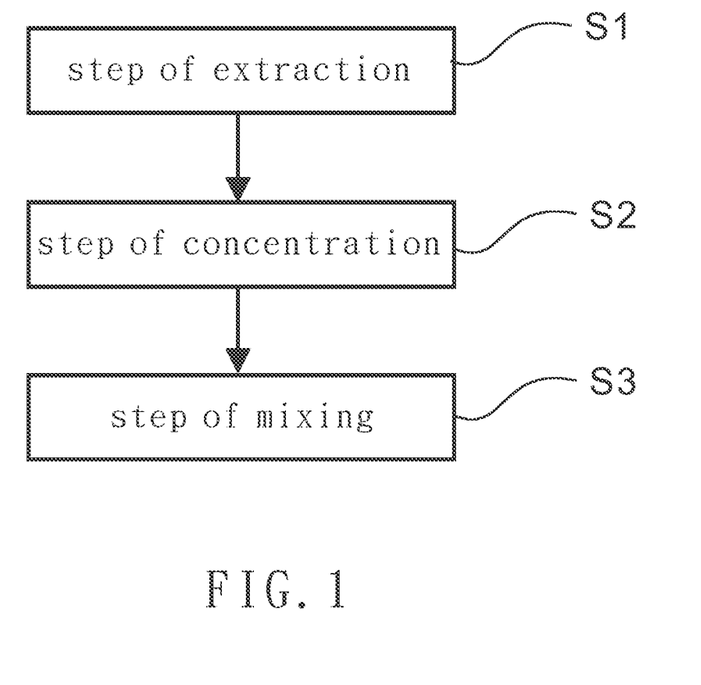
FIG. 1 is a diagram illustrating a method for preparing extracts of *Eucheuma okamurai* Yamada, *Acanthopanax senticosus* and *Dioscorea alata* of a composite of herbal extracts in a preferable embodiment of the present invention.

With reference to FIG. 1, the extract of *Eucheuma okamurai* Yamada, the extract of *Acanthopanax senticosus* and the extract of *Dioscorea alata* of the composite of herbal extracts of the preferable embodiment are obtained by using a method comprising steps of: extraction S1, condensation S2, and mixing S3.

In the step of extraction S1, samples of *Eucheuma okamurai* Yamada, *Acanthopanax senticosus* and *Dioscorea alata* are prepared and extracted respectively with water as a solvent, to obtain a liquid extract of *Eucheuma okamurai* Yamada, a liquid extract of *Acanthopanax senticosus* and a liquid extract of *Dioscorea alata*, wherein the solvent and the samples of *Eucheuma okamurai* Yamada, *Acanthopanax senticosus* and *Dioscorea alata* respectively being 1 to 8-1 to 12. Preferably, the solvent is mixed with the samples of *Eucheuma okamurai* Yamada, *Acanthopanax senticosus* and *Dioscorea alata* respectively in a weight ratio of 1:5, to promote extracting efficiency of the solvent without causing any waste of the solvent, and to reduce a use of the solvent, as well as the cost thereof in the step of extraction S1.

In the present embodiment, the sample of *Eucheuma okamurai* Yamada is selected from whole plant of *Eucheuma okamurai* Yamada, wherein a primary active substance in the *Eucheuma okamurai* Yamada is polysaccharide (500 daltons), being a polymer of monosaccharides, including xylose and galactose. The sample of *Acanthopanax senticosus* is selected from roots and stems of *Acanthopanax senticosus*, with syringin being primary active substance therein. The sample of *Dioscorea alata* is selected from root tubers of *Dioscorea alata* L. cv. Tainong 1 or *D. alata* L. cv. Tainong 2, with diosgenin being primary active substance therein.

Specifically, the samples of *Eucheuma okamurai* Yamada, *Acanthopanax senticosus* and *Dioscorea alata* can be selected from fresh samples that have not dried or solarized, dried samples, or decocted samples, with levels of active substances in the said three samples being increased. As an example, the sample of *Eucheuma okamurai* Yamada of the present embodiment is selected from a dry sample of *Eucheuma okamurai* Yamada that has been lyophilized for 24 hours; the sample of *Acanthopanax senticosus* of the present embodiment is selected from a decocted sample of *Acanthopanax senticosus* that has been stir-fried with wine, with 1 kg the sample of *Acanthopanax senticosus* being soaked in 200 ml huangjiu (a kind of yellow rice wine) for 8 hours, and then decocted at 121° C., 15 pound/itch$^2$ for 1 hour; and the sample of *Dioscorea alata* of the present embodiment is selected from a dry sample that has been heat-dried for 24 hours at 50° C. A process of decocting will increase the release of syringin and diosgenin from the samples of *Acanthopanax senticosus* and *Dioscorea alata* respectively.

In the present embodiment, the step of extraction is carried out at 40-60° C., for 6-10 hours, so that, the active substances in each herbal sample (including *Eucheuma okamurai* Yamada, *Acanthopanax senticosus*, and *Dioscorea alata*) will not be degraded due to high temperature but release in the solvent. Furthermore, the said herbal samples are preferably to be soaked in the solvent and shacked, in order to promote the release rate of the active substances in the solvent. With such performance, active substances of *Eucheuma okamurai* Yamada, *Acanthopanax senticosus*, and *Dioscorea alata*, being capable of lowering blood lipid, are successfully extracted and obtained from the liquid extract, which can be further manufactured into a medication for lowering blood lipid.

In the present embodiment, the solvent is selected from water, with dry samples of *Eucheuma okamurai* Yamada, *Acanthopanax senticosus*, and *Dioscorea alata* being extracted respectively at 50° C. for 8 hours, followed by removing residues of the dry samples of *Eucheuma okamurai* Yamada, *Acanthopanax senticosus*, and *Dioscorea alata* respectively, and obtaining the liquid extract of *Eucheuma okamurai* Yamada, *Acanthopanax senticosus*, and *Dioscorea alata*. Accordingly, the active substances of *Eucheuma okamurai* Yamada, *Acanthopanax senticosus*, and *Dioscorea alata* that is capable of lowering blood lipid, are successfully extracted and obtained from the liquid extracts of *Eucheuma okamurai* Yamada, *Acanthopanax senticosus*, and *Dioscorea alata* respectively.

In the step of condensation S2, the liquid extracts of *Eucheuma okamurai* Yamada, *Acanthopanax senticosus*, and *Dioscorea alata* are condensed respectively to obtain an extract of *Eucheuma okamurai* Yamada, an extract of *Acanthopanax senticosus*, and an extract of *Dioscorea alata*. As an example, the step of condensation S2 is but not limit to process via decompressed concentration, vapor, or heat-drying. In the present embodiment, the step of condensation S2 is carried out by heat-drying the said liquid extracts of *Eucheuma okamurai* Yamada, *Acanthopanax senticosus*, and *Dioscorea alata* respectively, removing the solvent therein and obtaining the extracts of *Eucheuma okamurai* Yamada, *Acanthopanax senticosus*, and *Dioscorea alata*. In this way, the efficiency of the active substances of *Eucheuma okamurai* Yamada, *Acanthopanax senticosus*, and *Dioscorea alata* in the extracts can be significantly promoted.

In the step of mixing S3, the extracts of *Eucheuma okamurai* Yamada, *Acanthopanax senticosus*, and *Dioscorea alata* are mixed to obtain a composite of herbal extracts, with the extract of *Eucheuma okamurai* Yamada in a weight ratio of 33.4%-77.7%, the extract of *Acanthopanax senticosus* in a weight ratio of 11.14%-33.3%, and the extract of *Dioscorea alata* in a weight ratio of 11.14%-33.3%. Precisely, 71.4% the extract of *Eucheuma okamurai* Yamada is mixed with 14.3% the extract of *Acanthopanax senticosus* and 14.3% the extract of *Dioscorea alata*. In this way, the said herbal extracts (including *Eucheuma okamurai* Yamada, *Acanthopanax senticosus*, and *Dioscorea alata*) will not interfere with each other, but cooperate with each other to achieve significant effects on controlling blood lipid via synergism. Hence, the composite of herbal extracts in the preferable embodiment of the present invention is capable of lowing the levels of TC, TG, or LDL-C in blood and reducing fat-accumulation in adipocytes, so as to reduce incidences to cardiovascular disease.

The composite of the preferable embodiment in the present invention can be further combined with a pharmaceutical acceptable carrier or excipient to manufacture into a medication, preferable a medication in an oral type, such as pastil, capsule, powder, pellet or solution. Yet, the said composite can be mixed with other food products or drinks, performing in a preferably oral type, so as to be easily given to organisms via oral.

For proving the composite of the preferable embodiment in the present invention truly having efficacies on controlling blood lipid and avoiding fat-accumulation, several composite, comprising the extracts of *Eucheuma okamurai* Yamada, *Acanthopanax senticosus*, and *Dioscorea alata* in various weight ratios are prepared to conduct a serial of trials. With such trials validate that the said composite of the preferable embodiment is sufficient to control the levels of TC, TQ high-density lipoprotein cholesterol (HDL-C), and LDL, and avoiding fat-accumulation in adipocytes.

Trial of (A)

In the present trial, a strain of adipocyte 3T3-L1 (BCRC 60159) is purchased from Food Industry Research and Development Institute in Taiwan, and co-cultured with various composites comprising different herbal extracts in various weight ratios or with a composite at various concentrations respectively.

With reference to Table 1, the strain of adipocyte 3T3-L1 are randomly assigned to 11 groups (including A1-1 to A1-11, with A1-1 being a control), with each groups comprising $1\times10^4$ cells/ml, incubated at 37° C., with 5% $CO_2$ for 24 hours, and then co-cultured with various composites respectively for 24 hours. After that, adipocytes in each group are dyed by oil red stain, with oil red staining neutral triglycerides and lipids in adipocytes on frozen sections, and thus that the level of fat-accumulation in each group can be observed and quantified.

TABLE 1

Groups Assignment in the Trial of (A)

Figure 2:
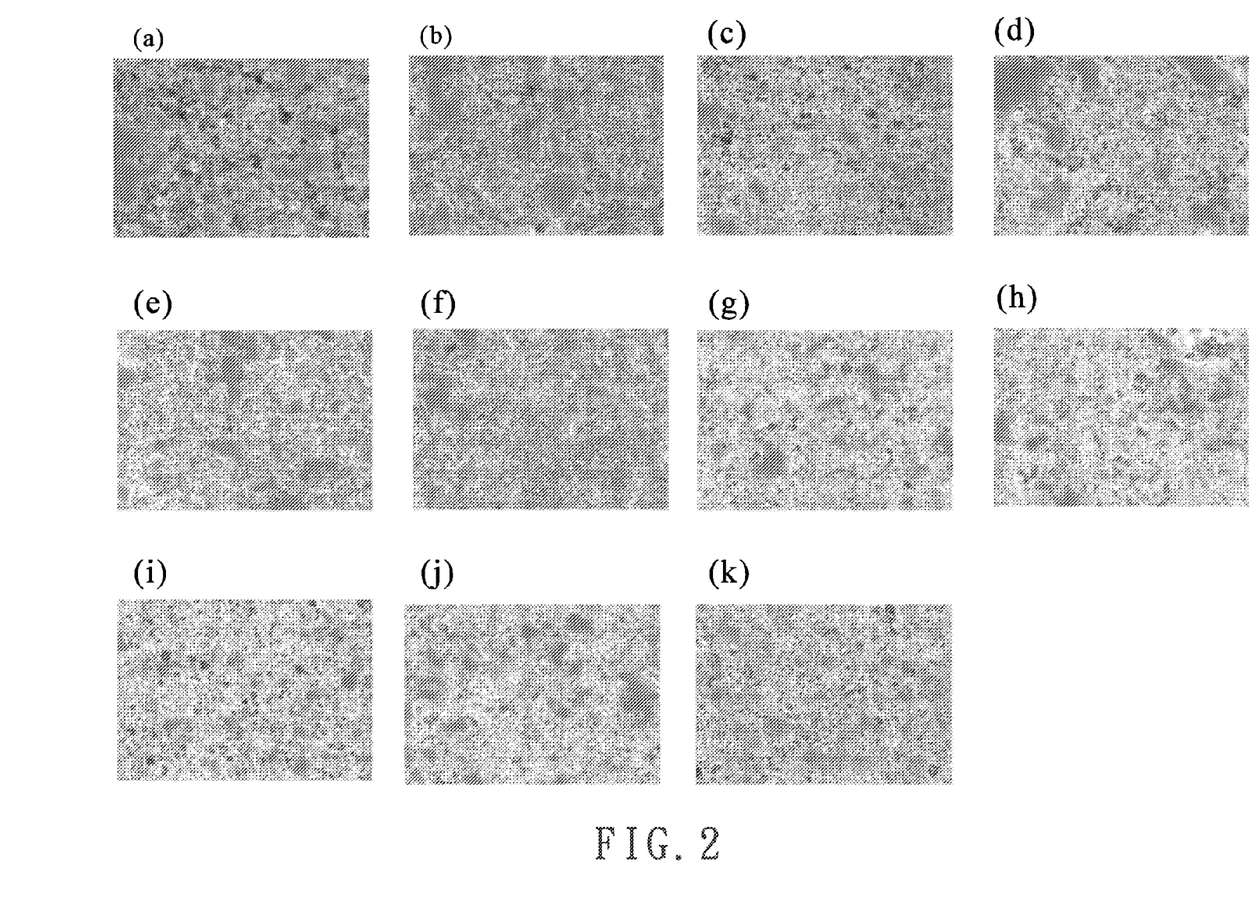
FIGS. 2a-k are photos illustrating adipocyte of groups A1-1 to A1-11 respectively under oil red dyed.

| Groups | Composites (500 µg/ml) (*Eucheuma okamurai* Yamada: *Acanthopanax senticosus*: *Dioscorea alata*) | FIGS. |
| --- | --- | --- |
| A1-1[a] | water | FIG. 2a |
| A1-2 | 1:0:0 | FIG. 2b |
| A1-3 | 0:1:0 | FIG. 2c |
| A1-4 | 0:0:1 | FIG. 2d |
| A1-5 | 1:1:1 | FIG. 2e |
| A1-6 | 2:1:1 | FIG. 2f |
| A1-7 | 3:1:1 | FIG. 2g |
| A1-8 | 4:1:1 | FIG. 2h |
| A1-9 | 5:1:1 | FIG. 2i |
| A1-10 | 6:1:1 | FIG. 2j |
| A1-11 | 7:1:1 | FIG. 2k |

[a]Group A1-1 is a control, with the adipocytes therein being cultured with water only.

Referring to FIGS. 2a to 2k, adipocytes in the groups A1-1 (FIG. 2a) show an oil-red-stained area being significantly larger than that of other groups; adipocytes in the groups A1-2, A1-3, A1-4 (FIGS. 2b, 2c and 2d), being cultured in 500 µg/ml the extract of *Eucheuma okamurai* Yamada, 500 µg/ml the extract of *Acanthopanax senticosus*, and 500 µg/ml the extract of *Dioscorea alata* respectively, have less amount of lipids in comprison with the group A1-1 but still higher than that of the groups A1-5 to A1-11.

Figure 3:
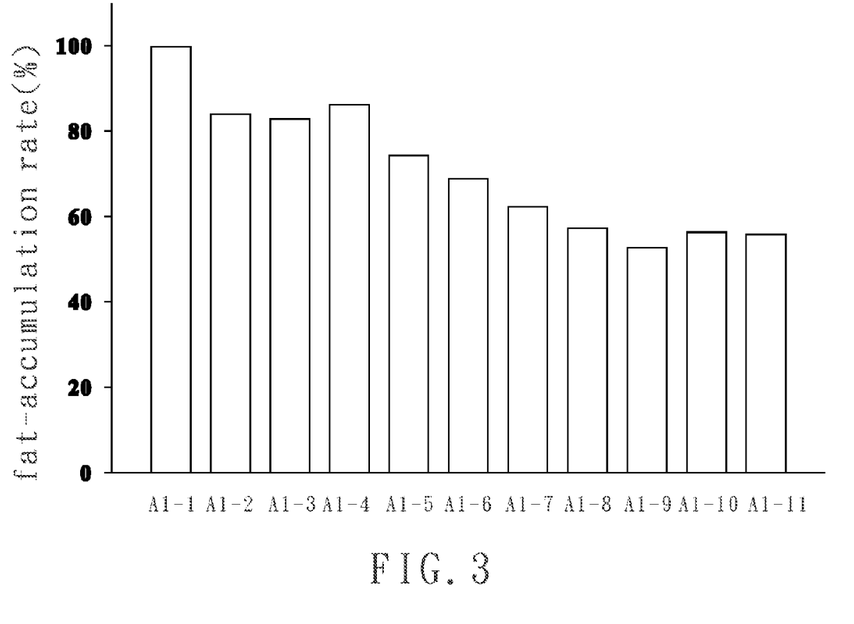
FIG. 3 is a bar chart illustrating fat-accumulation rates of groups A1-1 to A1-11.

In FIG. 3, the quantification of lipids in each groups are shown, with a fat-accumulation rate in the group A1-1 being set as benchmark (100%). It is noted that levels of lipids in the groups A1-5 to A1-11 are significantly lower than that in the groups A1-1 to A1-4. Accordingly, it is suggested that the composite of herbal extracts of the preferable embodiment in the present avoids fat-accumulation in adipocytes via synergism of the extracts of *Eucheuma okamurai* Yamada, *Acanthopanax senticosus*, and *Dioscorea alata*.

In additional, with reference to Table 2, the strain of adipocyte 3T3-L1 are further assigned to 8 groups (including A2-1 to A2-8, with A2-1 being a control), with each groups comprising $1\times10^4$ cells/ml, incubated at 37° C., with 5% $CO_2$ for 24 hours, and then co-cultured with a composites (comprising the extracts of *Eucheuma okamurai* Yamada, *Acanthopanax senticosus*, and *Dioscorea alata* in a weight ratio of 5:1:1) at various concentrations respectively for 24 hours. After that, adipocytes in each group are dyed by oil red stain, with oil red staining neutral triglycerides and lipids in adipocytes on frozen sections, and thus that the level of fat-accumulation in each group can be observed and quantified.

TABLE 2

Groups Assignment in the Trial of (A)

| Groups | Concentration of Composite (*Eucheuma okamurai* Yamada: *Acanthopanax senticosus*: *Dioscorea alata* = 5:1:1) |
|---|---|
| A2-1[a] | Water |
| A2-2 | 100 μg/ml |
| A2-3 | 200 μg/ml |
| A2-4 | 300 μg/ml |
| A2-5 | 400 μg/ml |
| A2-6 | 500 μg/ml |
| A2-7 | 600 μg/ml |
| A2-8 | 700 μg/ml |

[a]Group A2-1 is a control, with the adipocytes therein being cultured with water only.

Figure 4:
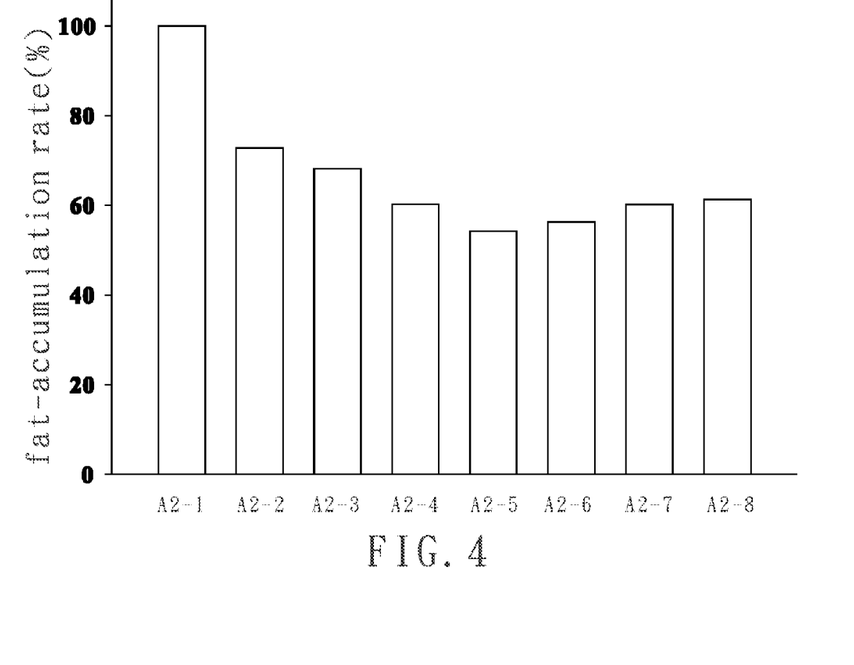
FIG. 4 is a bar chart illustrating fat-accumulation rates of groups A2-1 to A2-8.
Figure 5:
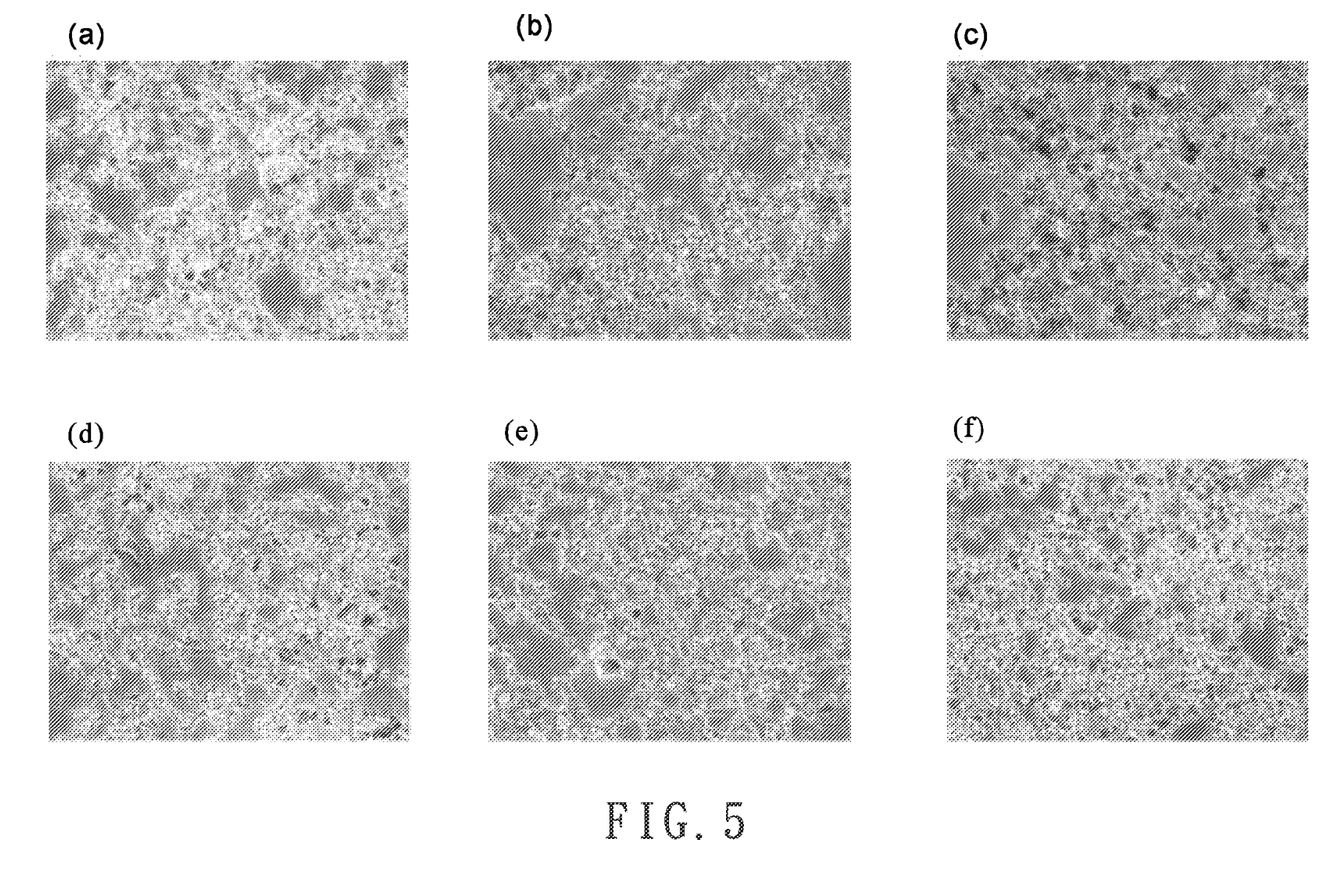
FIG. 5a is a photo illustrating adipocyte of groups A2-1 in 3 days after culturation.
FIG. 5b is a photo illustrating adipocyte of groups A2-1 in 6 days after culturation.
FIG. 5c is a photo illustrating adipocyte of groups A2-1 in 8 days after culturation.
FIG. 5d is a photo illustrating adipocyte of groups A2-5 in 3 days after culturation.
FIG. 5e is a photo illustrating adipocyte of groups A2-5 in 6 days after culturation.
FIG. 5f is a photo illustrating adipocyte of groups A2-5 in 8 days after culturation.
Figure 6:
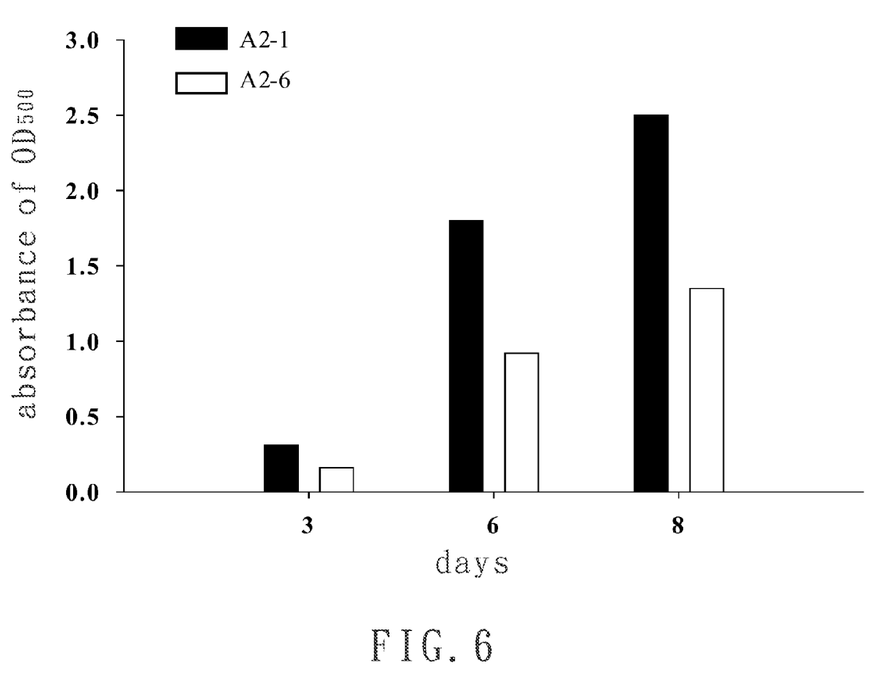
FIG. 6 is a bar chart illustrating absorbance of adipocytes in groups A2-1 and A2-5 under $OD_{500}$ in 3, 6, 8 days after culturation.

With reference to FIG. 4, the quantification of lipids in each groups are illustrated, wherein a fat-accumulation rate in the group A1-1 is set as benchmark (100%). It is shown that levels of lipids in the groups A2-2 to A2-8 (have been cultured with the composite at 100~700 μg/ml respectively) are significantly lower than that in the groups A2-1.

In FIGS. 5a to 5f and 6, accumulations of lipids in adipocytes of the groups A2-1, A2-2, A2-3, A2-4, A2-5 and A2-6 in 3, 6 and 8 days after the co-culturation are shown respectively. It is believed that the composite of herbal extracts of the preferable embodiment in the present invention truly can avoid fat-accumulation in adipocytes via synergism of the extracts of *Eucheuma okamurai* Yamada, *Acanthopanax senticosus*, and *Dioscorea alata*, especially when the composite of herbal extracts comprises the extracts of *Eucheuma okamurai* Yamada, *Acanthopanax senticosus*, and *Dioscorea alata* in a weight ratio of 5:1:1.

Trial of (B)

In the present trial, male Golden Syrian hamsters purchased from National Laboratory Animal Center (National Research Center for Experimental Animal, Taiwan) are housed at a standard laboratory environment by keeping at 25±1° C., 12 hours light/dark cycle, and feeding normal diets and drinks till the Golden Syrian hamsters being 4-weeks-old, followed by giving high-fats diets (TestDiet® STJT, comprising 1% cholesterol) for 8 weeks (till the Golden Syrian hamsters being 12 weeks-old), to obtain high-fat diet induced hamsters (HFD hamsters). Yet, another group of Golden Syrian hamsters (group B0) are also prepared by hosting at the standard laboratory environment and feeding normal diet till being 12-weeks-old.

With reference to Table 3, the said HFD hamsters are randomly assigned to 4 groups (with each group comprising 8 hamsters) and fed with various diets for 8 weeks. After that, weights, and levels of TG, TC, HDL-C and LDL-C of the HFD hamsters in each group are monitored and recorded in the present trial. Precisely, the HFD hamsters in each group are tube-fed daily with various dosages (including 1.5, 3.0 and 6.0 g/per kg/day) of the composite of herbal extracts in the present invention (comprising the extracts of *Eucheuma okamurai* Yamada, *Acanthopanax senticosus*, and *Dioscorea alata* in a weight ratio of 5:1:1)

TABLE 3

Groups Assignment in the Trial of (B)

| Groups | Feeding Conditions | Weights (g) |
|---|---|---|
| B0 | Normal diets | 160.3 ± 6.8 |
| B1 | Water | 231.2 ± 8.7 |
| B2 | 1.5 g/kg/day the composite of herbals extracts | 201.4 ± 9.4[a] |
| B3 | 3.0 g/kg/day the composite of herbals extracts | 178.6 ± 6.7[a] |
| B4 | 6.0 g/kg/day the composite of herbals extracts | 155.0 ± 8.1[a] |

[a]$p < 0.05$

In Table 3, it is noted that the weights of the HFD hamsters in the groups B2-B4 is quick different from that of the HFD hamsters in the group B1 ($p<0.05$).

In Table 4, levels of lipid parameters (including TG, TC, HDL-C, and LDL-C) in the HFD hamsters of each group are summarized. It is shown that, levels of TC, TG and LDL-C in the HFD hamsters of the groups B2-B4 are reduced in a dose-depended manner in comparison with the group B1.

TABLE 4

Levels of Blood Lipids of the HFD Hamsters in Each Group

| Groups | TC (mg/dl) | TG (mg/dl) | HDL-C (mg/dl) | LDL-C (mg/dl) |
|---|---|---|---|---|
| B0 | 103.1 ± 6.4 | 70.6 ± 6.9 | 45.3 ± 4.1 | 34.9 ± 3.5 |
| B1 | 293.4 ± 6.6 | 253.6 ± 7.2 | 25.8 ± 5.3 | 141.1 ± 5.3 |
| B2 | 206.8 ± 5.8[a] | 211.7 ± 8.1[a] | 26.4 ± 4.2 | 138.3 ± 4.8 |
| B3 | 186.5 ± 4.7[a] | 190.6 ± 4.6[a] | 26.1 ± 3.9 | 122.4 ± 4.5[a] |
| B4 | 173.4 ± 6.2[a] | 178.4 ± 5.8[a] | 25.9 ± 5.1 | 111.8 ± 5.1[a] |

[a]$p < 0.05$

Accordingly, it is believed that giving the said composite of herbal extracts to the HFD hamsters in a dosage of 1.5~6.0 g/kg/day can reduce the level of blood lipid and weight of the HFD hamsters. Also, with data of the Table 4, it is suggested that a preferable dosage of the composite of herbal extracts for an adult (60 kg) is 150-600 mg/per days.

In summary, the composite of herbal extracts of the preferable embodiment in the present invention combines active substances obtained from three natural plants, including *Eucheuma okamurai* Yamada, *Acanthopanax senticosus*, and *Dioscorea alata*, with the extracts of *Eucheuma okamurai* Yamada, *Acanthopanax senticosus*, and *Dioscorea alata* avoiding fat-accumulation in adiocytes, controlling blood parameters (TG, TC, and LDL-C) of animal suffered from hyperlipidemia. The composite of herbal extracts of the preferable embodiment of the present invention comprises the said three extracts in a particular ratio, so that each extract will not interfere with each other but achieve significant effects on lowering blood lipid via synergism.

The composite of herbal extracts of the preferable embodiment in the present invention in a preferable dosage (150-600 mg/per day) can be further combined with a pharmaceutical acceptable carrier or excipient to manufacture into a medication. The said composite of herbal extracts is prepared by using a method disclosed in FIG. 1. Preferably, the said composite of herbal extracts is given to an individual in a dosage of 150-600 mg/per kg for 8 weeks, to control the lipid parameters and to avoid fat-accumulation in adipocytes. Moreover, the active substances in the said medication are obtained from natural plants, including *Eucheuma okamurai* Yamada, *Acanthopanax senticosus*, and *Dioscorea alata*, being safe and non-toxic to organisms. Therefore, the said medication will not cause hepatotoxic to users, so that it can be easily acceptable to generally public.

The composite of herbal extracts of the preferable embodiment in the present invention has efficacies on controlling lipid parameters, avoiding fat-accumulation in adiocytes, and further reducing incidence to cardiovascular disease.

The said composite of herbal extracts, as well as the medication comprising the said composite of herbal extracts is capable of avoiding fat-accumulation in adiocytes via synergism, significantly achieving a efficacy on lower blood lipids.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A composite of herbal extracts comprising:
   an extract of *Eucheuma okamurai* Yamada in a weight ratio of 33.4%-77.7%;
   an extract of *Acanthopanax senticosus* in a weight ratio of 11.14%-33.3%; and
   an extract of *Dioscorea alata* in a weight ratio of 11.14%-33.3%.

2. The composite of herbal extracts as claimed in claim 1, wherein the extract of *Eucheuma okamurai* Yamada, the extract of *Acanthopanax senticosus* and the extract of *Dioscorea alata* are obtained by using a method comprising:
   extracting samples of *Eucheuma okamurai* Yamada, *Acanthopanax senticosus* and *Dioscorea alata* respectively with a solvent, with the volume of solvent to anyone of the samples of *Eucheuma okamurai* Yamada, *Acanthopanax senticosus* and *Dioscorea alata* at a ratio of 1 to 8-12, to obtain a liquid extract of *Eucheuma okamurai* Yamada, a liquid extract of *Acanthopanax senticosus* and a liquid extract of *Dioscorea alata*; and
   condensing the liquid extract of *Eucheuma okamurai* Yamada, the liquid extract of *Acanthopanax senticosus* and the liquid extract of *Dioscorea alata* respectively to obtain the extract of *Eucheuma okamurai* Yamada, the extract of *Acanthopanax senticosus* and the extract of *Dioscorea alata*; wherein, the solvent is water.

3. The composite of herbal extracts as claimed in claim 2, wherein the samples of *Eucheuma okamurai* Yamada, *Acanthopanax senticosus* and *Dioscorea alata* are fresh samples that have not been dried or solarized, dry samples or decocted samples.

4. The composite of herbal extracts as claimed in claim 3, wherein the sample of *Acanthopanax senticosus* in 1 kg is soaked in 200 ml Chinese yellow rice wine huangjiu for eight hours, and then decocted at 121° C., 15 pound/inch$^2$ for one hour, to obtain a decocted sample of *Acanthopanax senticosus*.

5. The composite of herbal extracts as claimed in claim 3, wherein the sample of *Eucheuma okamurai* Yamada is lyophilized to obtain a dry sample of *Eucheuma okamurai* Yamada.

6. The composite of herbal extracts as claimed in claim 3, wherein the sample of *Dioscorea alata* is heat-dried to obtain a dry sample of *Dioscorea alata*.

7. The composite of herbal extracts as claimed in claim 2, wherein the sample of *Eucheuma okamurai* Yamada in the extracting comprises whole plant of *Eucheuma okamurai* Yamada.

8. The composite of herbal extracts as claimed in claim 2, wherein the sample of *Acanthopanax senticosus* in said extracting comprises roots and stems of *Acanthopanax senticosus*.

9. The composite of herbal extracts as claimed in claim 2, wherein the sample of *Dioscorea alata* in said extracting comprises root tubers of *Dioscorea alata*.

10. The composite of herbal extracts as claimed in claim 2, wherein said extracting is processed at 40° C.-60° C.

11. The composite of herbal extracts as claimed in claim 2, wherein said extracting is processed for six to ten hours.

12. A medication for lowering blood lipid, comprising:
    the composite of herbal extracts as claimed in claim 1; and
    a pharmaceutical acceptable carrier or excipient.

13. The medication for lowering blood lipid as claimed in claim 12, wherein the composite of herbal extracts is in a dosage of 150-600 mg.

14. The medication for lowering blood lipid as claimed in claim 12, wherein the composite of herbal extracts is in a form of paste, capsule, powder, pellet or solution.

* * * * *